(12) United States Patent
Hofrichter et al.

(10) Patent No.: US 7,046,379 B2
(45) Date of Patent: May 16, 2006

(54) METHOD FOR CHARACTERIZING OR CONTROLLING THE PRODUCTION OF A THIN-LAYERED COMPONENT USING OPTICAL METHODS

(75) Inventors: Alfred Hofrichter, Paris (FR); Bernard Drevillon, Clamart (FR); Dmitri Kouznetsov, Palaiseau Cedex (FR)

(73) Assignees: Centre National de la Recherche Scientifique (C.N.R.S.), Paris (FR); Jobin Yvon S.A., Longjumeau (FR)

( * ) Notice: Subject to any disclaimer, the term of this patent is extended or adjusted under 35 U.S.C. 154(b) by 292 days.

(21) Appl. No.: 10/470,994

(22) PCT Filed: Jan. 31, 2002

(86) PCT No.: PCT/FR02/00380

§ 371 (c)(1),
(2), (4) Date: Jan. 12, 2004

(87) PCT Pub. No.: WO02/061401

PCT Pub. Date: Aug. 8, 2002

(65) Prior Publication Data

US 2004/0114131 A1    Jun. 17, 2004

(30) Foreign Application Priority Data

Feb. 1, 2001   (FR) ................... 01 01377

(51) Int. Cl.
*G01B 11/28*   (2006.01)

(52) U.S. Cl. ...................... 356/630; 356/632

(58) Field of Classification Search ............... 356/630, 356/632
See application file for complete search history.

(56) References Cited

U.S. PATENT DOCUMENTS 5,900,633 A * 5/1999 Solomon et al. ....... 250/339.08

* cited by examiner

*Primary Examiner*—Gregory J. Toatley, Jr.
*Assistant Examiner*—Roy M. Punnoose
(74) *Attorney, Agent, or Firm*—Young & Thompson

(57) ABSTRACT

A method for characterizing or controlling the production of a thin-layered component using optical methods. Acquired signals S1 and S2 are processed in order to obtain parameters x, $\in$ of the deposited layers. The stacking is represented by the product of two Abeles matrices for each direction of polarization s (perpendicular to the incidence plane) and p (parallel to the incidence plane): a known matrix $Mo_{s,p}$ representing the support and matrix $dM_{s,p}$ representing a thin transparent layer being deposited. The signal variations measured, $dS_1$ and $dS_2$, are inverted to obtain thickness x and dielectric constant $\in$ of the thin layer by the following operations: Taylor expansion as a function of variation dx of thickness x of the thin layer of the coefficients of matrix dM; the coefficients of matrix $M_{s,p}$ are calculated each in the form $A(\in^{\pm 2})dx^2+B(\in^{\pm 1})dx+C$ and the relation $S_{1,2}=A_{1,2}(\in^{\pm 2})\ dx^2+B_{1,2}(\in^{\pm 1})\ dx+C_{1,2}$ is thereby deduced which connects signals $S_1$ and $S_2$ to parameters $\in$ and dx; dx is eliminated and a master function $P(\in^{\pm 4})=0$ is thereby deduced; the equation is solved and the solutions are selected corresponding to values that are physically plausible in order to measure $\in$ and use the $\in$ value obtained to determine dx.

15 Claims, 4 Drawing Sheets

METHOD FOR CHARACTERIZING OR CONTROLLING THE PRODUCTION OF A THIN-LAYERED COMPONENT USING OPTICAL METHODS

BACKGROUND OF THE INVENTION

The present invention relates to a characterisation or control method for preparation of a thin layer component by optical methods.

For the production of high quality optical layers, increased control of the preparation of each layer and of its refraction index has become a crucial challenge. Among the different control method, it is well known that ellipsometry is one of the most sensitive. It has therefore been contemplated to compare in real time the evolution of ellipsometric parameters $I_s$, $I_c$, or any other combination of these parameters with respect to a theoretical evolution.

It has been suggested to compare the distance between points which are respectively theoretical and measured, represented in a referential $I_s$, $I_c$ or still the lengths of the travelled paths measured.

It is, moreover, useful to have a reliable method for characterising the optical layers deposited. Then two possible aspects should be considered according to the usage made of the characterisation method. A dynamic aspect where after each new layer deposited of thickness dx, the layers deposited are characterised by measuring for instance optical signals $S_1$ and $S_2$. These signals enable then to get for instance the control parameter $\in$ of the layers deposited. $\in$ is the dielectric constant of the layer with $\in = n^2$ where n is the optical index. If $\in$ is equal to the value $\in'$ required, the following layer is deposited without re-adjusting the deposition parameters. Failing which, said parameters are adjusted in order to correct the error. The deposition parameters may thus be corrected in real time for optimised control of the deposition.

Such a method may also be used to characterise the evolution of the refraction index in relation to deposition parameters, without implementing any control of deposition. With reference to the fitting of the curve providing the variations of the dielectric constant $\in$ as a function of these parameters, the parameters necessary to the production of a layer with a given index can be found. Such characterisation thus enables to minimise the number of cycles of deposition/ characterisation necessary for the production of a layer with a given index.

Various direct digital reversal methods have thus been developed, but have prove suitable only for relatively thick films (200–500 Å). Others, based fitting methods seem more efficient, but have the disadvantage of requiring-tedious calculations and correction methods in order to stabilise the variation of the refraction index.

Approximations have however been suggested in order to simplify these calculations. It may be judicious, for instance, to reduce the number of parameters necessary to the fitting ("dispersion laws" [Heitz T and al.; J. Vac. Sci. Technol. A 18 (2000) 1303–1307], "Effective medium approximations" [Kildemo and al.; Applied Optics 37 (1998), 5145–5149]) or reduce, using suitable optical approximations the problems encountered when calculating the optical film (WKBJ, multiple integral methods, etc. [Kildemo and al.; Applied Optics 37, (1998) 113–124]).

However, these methods are too complex to be implemented in real time and in various situations such as those which are indeed encountered when producing the stacks of layers.

Besides, polynomial methods are known for reversing the ellipsometric signal [Lekner, J and al.; Applied Optics 33 (1994) 5159–5165; Drolet, J. P. and al.; Opt. Soc. Am. A 11 (1994) 3284–329]. These methods are, nevertheless, applicable only to non-absorbent monolayer and to samples exhibiting very simple structures. They use, moreover, the ellipsometric angles $\psi$ and $\Delta$ as input parameters for the reversal formulae. Still, these values cannot be obtained directly by most ellipsometers.

BRIEF SUMMARY OF THE INVENTION

The purpose of the invention consists thus in providing a characterisation or control method of the preparation of a component made of thin layers which is based on a direct reversal principle, enabling to access the physical parameters of the layer (its thickness x and its dielectric constant $\in$) in real time using the parameters measured in real time by an optical instrument.

This requires an approach and approximations which are part of the invention.

In this view, the invention relates to a characterisation or control method for preparation of a thin layer component according to optical methods wherein:
 the parameters $S_1$ and $S_2$ related to the thickness x and to the complex optical index of the component are measured and acquired for at least a wavelength $\lambda$,
 the signals $S_1$ and $S_2$ thus acquired are processed in order to obtain the parameters x, $\in$ of the layers deposited.

According to the invention:
 the stacking is represented by the product of two Abeles matrices for each polarisation direction s (perpendicular to the plane of incidence) and p (parallel to the plane of incidence):
  a matrix $Mo_{s,p}$ known representing the support,
  a matrix $dM_{s,p}$ representing a thin transparent layer being deposited,
 reversing the variations of the measured signals $dS_1$, $dS_2$ enables to get the thickness x and the dielectric constant $\in$ of the thin layer using the following operations:
  Taylor development in relation to the variation dx of the thickness x of the thin layer of the coefficients of the matrix dM,
  calculating the coefficients of the matrix $M_{s,p}$ each in the form $A(\in^{\pm 2})dx^2 + B(\in^{\pm 1})dx + C$ deducing therefrom the relation $S_{1,2} = A_{1,2}(\in^{\pm 2})dx^2 + B_{1,2}(\in^{\pm 1})dx + C_{1,2}$ linking the signals $S_1$ and $S_2$ to the parameters $\in$ and dx,
 eliminating dx
 deducing therefrom a master function $P(\in^{\pm 4}) = 0$ solving the equation using an appropriate method,
 selecting the solutions of this equation corresponding to values physically plausible, to measure $\in$,
 using the value $\in$ obtained to determine dx.

The present invention also relates to the features which will appear during the following description and which should be considered individually or in all their technically possible combinations:
 the Taylor development is limited to the second order,
 said method is applied during the deposition of the stacking and the evolution of $\in$ and/or $x_o$ is recorded, said method is applied during the deposition of the stacking and the conditions of the deposition are influenced to interlock the parameters $\in$, x of the layers with preset theoretical values, the ellipsometer is phase-modulated generating the parameters $I_s$ and $I_c$, the ellipsometer is fitted with a rotary polariser generating the parameters tan ψ, cos Δ, the thin layer is transparent, the thin layer is absorbent, the measurement is multiwavelength, the thickness is optimised by averaging over the different wavelengths, after optimising the thickness, the complex indices are recalculated, if one of the measured signals $S_1$, $S_2$ is unusable, the other of the terms S1, S2 is developed to the second order in relation to time in the relation $S_1$, $S_2 = A_{1,2}(\in^{\pm 2})dx^2 + B_{1,2}(\in^{\pm 1})dx + C_{1,2}$ in order to determine new master function $P(\in^{\pm 2}) = 0$, if the deposition rate in the initial conditions of deposition is unknown or is not constant during the deposition, the value of the reversing pitch is adapted dynamically, for a film exhibiting a low absorption rate, attempt is made to minimise the deviation between required and reconstructed theoretical values, if no value is obtained for a given wavelength λ, the values of the indices $\in$ obtained are processed statistically for various wavelengths close to λ to deduce therefrom the value of $\in$ for the wavelength λ considered.

DESCRIPTION OF THE DRAWINGS

The invention will be illustrated with reference to the appended drawings whereon the results are compared for the reconstruction of reflection index profiles during plasma deposition.

DETAILED DESCRIPTION OF THE INVENTION

Figure 1:
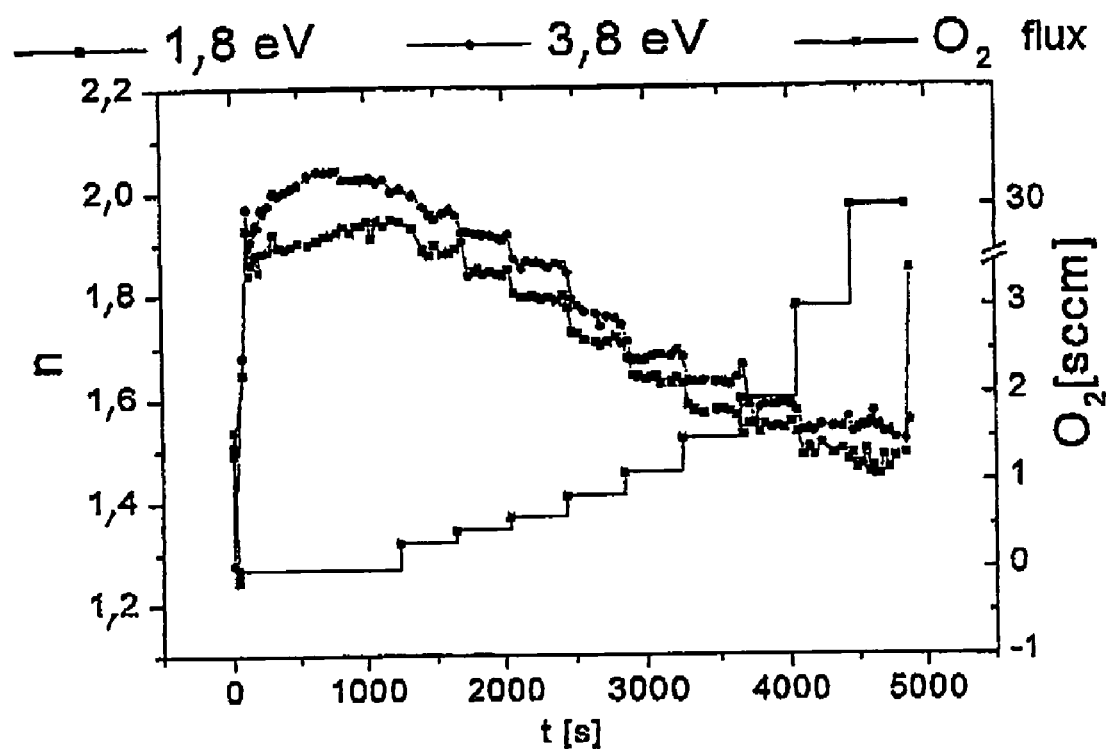
FIG. 1 represents the evolution of the molecular oxygen flux and of the refraction index reconstructed as a function of the deposition time for two different wavelengths.

It is known that the optical response of a layer i to a polarisation light excitation, respectively s and p, may be represented by two matrices, so-called "Abeles matrices" $M_i$, the thickness of the layer being x and its complex index $\in_i$ [Abeles, F.; Annales de Physique 5 (1950) 596–640; 706–782].

The Abeles matrix has then the following form:

$$M_i = \begin{pmatrix} \cos\varphi_i & \dfrac{i}{q_i}\sin\varphi_i \\ iq_i\sin\varphi_i & \cos\varphi_i \end{pmatrix}$$

where $\varphi_i = k\sqrt{\in_i - \alpha^2}\, x_i$, $k = 2\pi/\lambda$ being the wave number.

For the polarisation s (perpendicular to the plane of incidence)

$$q_i = \frac{\varepsilon_i}{\sqrt{\varepsilon_i - \alpha^2}},$$

for the polarisation p (parallel to the plane of incidence) $q_i = \sqrt{\in_i - \alpha^2} = \tilde{n}_i \cos\gamma_i$ where $\gamma_i$ is the angle of propagation in the layer i.

α is linked to the dielectric constant $\in$ and to the angle of incidence $\gamma_i$ by the following formula:

$$\alpha = \sqrt{\in_a} \sin\gamma_a = \sqrt{\in_i} \sin\gamma_i$$

where a and i signify respectively "ambient" and "layer i".

The optical response of the whole multilayer stacking is represented by the matrix M, product of the individual matrices representative of each layer:

$$M = \begin{pmatrix} m_{11} & m_{12} \\ m_{21} & m_{22} \end{pmatrix} = \prod_{i=1}^{n} M_i \tag{1}$$

Finally, the Fresnel reflection coefficients (and similarly, the transmission coefficients) of the stacking may be calculated as follows:

$$r = \frac{q_a m_{11} - q_s m_{22} + q_a q_s m_{12} - m_{21}}{q_a m_{11} + q_s m_{22} + q_a q_s m_{12} + m_{21}} \tag{2}$$

where a and s signify respectively "ambient" and "substrate".

The method suggested according to the invention is based on the polynomial development of the coefficients of the Abeles transfer matrices for a layer deposited i. This digital reversal method, unlike previous polynomial methods, is not limited to a single layer i. It may, indeed, be used iteratively for characterisation of the multilayer films if the Abeles matrices M of the stacking of the layers whereon the layer i has been deposited, are known or if they may have been reconstructed according to the formula mentioned in (1).

The method, according to the invention, may be applied quite generally to any optical signal used in situ for controlling the deposition of thin layers. The optical signals $S_1$ and $S_2$ may then be derived from ellipsometric or photometric measurements as long as they consist of combinations of the complex Fresnel coefficients of reflection or transmission.

In the case of ellipsometric measurements, one may wish to determine the ratio $$\rho = \frac{r_p}{r_s} = \tan\Psi e^{i\Delta}$$

where $r_p$ and $r_s$ are the complex Fresnel coefficients.

It is then known that these parameters may be obtained by different types of measurements. The optical signals $S_1$ and $S_2$ measured may then be in relation to the optical instrument used, the following parameters:

| Optical instrument | Signal S1 | Signal S2 |
|---|---|---|
| Ellipsometry (ellipsometric angles) | $\psi$ | $\Delta$ |
| Phase-modulated ellipsometry | Is | Ic |
| Ellipsometry with rotating analyser | $\tan\psi$ | $\cos\Delta$ |
| Ellipsometry with rotating analyser and compensator | $\tan\psi$ | $\sin\Delta$ |
| Reflectometry with oblique angle of incidence | $R_p = r_p \cdot r_p^*$ | $R_s = r_s \cdot r_s^*$ |

Thus, for instance, in phase-modulated ellipsometry, in the configuration II the following measurements are made— when the modulator is oriented to 0°, the analyser to 45° and the angle between the polariser and the modulator is set to 45° [Drévillon B. Prog. Cryst. Growth Charact. Matter 27 (1993),1]:

$$I_s = \sin 2\psi \sin\Delta = 2\text{Im}\left(\frac{r_s^* r_p}{r_s r_s^* + r_p r_p^*}\right)$$

$$I_c = \sin 2\psi \cos\Delta = 2\text{Re}\left(\frac{r_s^* r_p}{r_s r_s^* + r_p r_p^*}\right)$$

which correspond to the first and second harmonics of the polarised light.

In the particular case of transparent layers on a substrate which is thick (>0,1 µm) and transparent, the reflection of the rear face of the substrate should be taken into consideration. In such a case, the phase coherence of the incident light is lost and depolarisation phenomena take place. Then, $r_{s,p}{}^* r_{s,p}$ should be replaced with products averaged along the optical path [Kildemo and al.; Thin Solid fims 313 (1998), 108]:

$$\langle r_{s,p} r_{s,p}^* \rangle = r_{s,p} r_{s,p}^* + \frac{(t_{s,p} t_{s,p}^*)(t'_{s,p} t'^*_{s,p})(r_{bs,p} r_{bs,p}^*) e^{-4Im\beta_s}}{1 - (r'_{bs,p} r'^*_{bs,p})(r_{bs,p} r_{bs,p}^*) e^{-4Im\beta_s}} \quad (3)$$

where $\beta_s$ is equal to $$2\pi \frac{x_s}{\lambda} \sqrt{\varepsilon_s^2 - \varepsilon_a^2 \sin^2\varphi_a} \, ,$$

$(t_{s,p})$ and $(t'_{s,p})$ are the transmission Fresnel coefficients of the stacking of layers, respectively in one direction and in the other and $x_s$ and $\in_s$ are the thickness and the dielectric constant of the substrate, a signifies "ambient".

In the case of a thin surface layer, whereof the thickness is dx, it is represented by the Abeles matrices dMs and dMp, respectively for the directions s and p of the incident polarisation, according to the following formulae:

$$dMs = \begin{bmatrix} \cos(k\sqrt{\varepsilon - \alpha^2} \cdot dx) & \frac{i}{\sqrt{\varepsilon - \alpha^2}} \cdot \sin(k\sqrt{\varepsilon - \alpha^2} \cdot dx) \\ i \cdot \sqrt{\varepsilon - \alpha^2} \cdot \sin(k\sqrt{\varepsilon - \alpha^2} \cdot dx) & \cos(k\sqrt{\varepsilon - \alpha^2} \cdot dx) \end{bmatrix} \quad (4)$$

$$dMp = \begin{bmatrix} \cos(k\sqrt{\varepsilon - \alpha^2} \cdot dx) & i \cdot \frac{\sqrt{\varepsilon - \alpha^2}}{\varepsilon} \cdot \sin(k\sqrt{\varepsilon - \alpha^2} \cdot dx) \\ i \cdot \frac{\varepsilon}{\sqrt{\varepsilon - \alpha^2}} \cdot \sin(k\sqrt{\varepsilon - \alpha^2} \cdot dx) & \cos(k\sqrt{\varepsilon - \alpha^2} \cdot dx) \end{bmatrix} \quad (5)$$

According to the invention, it is suggested to proceed to a Taylor development on the coefficients of these matrices, for instance of the second order, enabling to obtain:

$$dMs = \begin{bmatrix} 1 + \left[\frac{-1}{2} \cdot k^2 \cdot (\varepsilon - \alpha^2)\right] \cdot dx^2 & i \cdot k \cdot dx \\ i \cdot (\varepsilon - \alpha^2) \cdot k \cdot dx & 1 + \left[\frac{-1}{2} \cdot k^2 \cdot (\varepsilon - \alpha^2)\right] \cdot dx^2 \end{bmatrix} \quad (6)$$

$$dMp = \begin{bmatrix} 1 + \left[\frac{-1}{2} \cdot k^2 \cdot (\varepsilon - \alpha^2)\right] \cdot dx^2 & i \cdot \left(1 - \frac{1}{\varepsilon} \cdot \alpha 2\right) \cdot k \cdot dx \\ i \cdot \varepsilon \cdot k \cdot dx & 1 + \left[\frac{-1}{2} \cdot k^2 \cdot (\varepsilon - \alpha^2)\right] \cdot dx^2 \end{bmatrix} \quad (7)$$

It appears thus that the different coefficients of these matrices are in the form:

$$A(\in^{\pm 2}) \cdot dx^2 + B(\in^{\pm 1}) \cdot dx + C \quad (8)$$

where $A(\in^{\pm 2})$ and $B(\in^{\pm 1})$ are polynomials of $\in$ as follows:

$$B(\varepsilon^{\pm 1}) = C_1^B \varepsilon + C_0^B + \frac{C_{-1}^B}{\varepsilon} \quad (9)$$

$$A(\varepsilon^{\pm 2}) = C_2^A \varepsilon^2 + C_1^A \varepsilon + C_0^A + \frac{C_{-1}^A}{\varepsilon} + \frac{C_{-2}^A}{\varepsilon^2} \quad (10)$$

where $C_i^{A,B}$ are complex constants.

When the previous measurement(s) enable to access (or to reconstruct) digitally the coefficients of the matrices Ms, Mp, one may deduce therefrom (by simple matrix multiplication) the coefficients of the polynomials A and B of the matrices produced $$M_s^{prod} = dMs \cdot Ms, \; M_p^{prod} = dMp \cdot Mp$$

To then extract the reflection Fresnel coefficients as a function of $\in$ and dx, the coefficients of the matrices $M_{s,p}^{prod}$ in the formulae mentioned above (2) should be replaced.

The equations are obtained as follows:

$$r_{s,p}^{prod} = \frac{A(\varepsilon^{\pm 2})dx^2 + B(\varepsilon^{\pm 1})dx + C}{A'(\varepsilon^{\pm 2})dx^2 + B'(\varepsilon^{\pm 1})dx + C'}$$

By dividing these polynomials and by keeping only the terms of the second order, an expression as follows can be obtained:

$$r_{s,p}^{prod} \approx r_{s,p} + dr_{s,p} = C + A(\in^{\pm 2}) \cdot dx^2 + B(\in^{\pm 1}) \cdot dx \quad (11)$$

where $r_{s,p}$ are the reflection coefficients of the stacking before the layer being deposited and $dr_{s,p}$ represents the changes in the reflection properties introduced by this layer being deposited.

It may then be noticed that C is identical to $r_{s,p}$ which is the reflection coefficient of the stacking before deposition of the last layer.

To link these formulae to the optical parameters measured, $S_1$ and $S_2$, one should introduce the coefficients of these polynomials in one of the equations mentioned according to the type of measurements defined on the table of page 7.

By using suitable formulae, one may finally express the signal measured in relation to dx, $dx^2$ and of polynomials depending essentially on $\in$:

$$dS_1 = A_1(\in^{\pm 2}) \cdot dx^2 + B_1(\in^{\pm 1}) \cdot dx \quad (12)$$

$$dS_2 = A_2(\in^{\pm 2}) \cdot dx^2 + B_2(\in^{\pm 1}) \cdot dx \quad (13)$$

which is simple in the case of transparent materials $\in_i = 0$.

When $dS_1$ and $dS_2$ are known experimentally, it is possible to introduce them in the previous equations and dx may be expressed in two different ways in relation to polynomials of $\in$:

$$dx_1 = \frac{dS_1 \cdot B_2 - dS_2 \cdot B_1}{dS_2 \cdot A_1 - dS_1 \cdot A_2} = \frac{T(\varepsilon^{\pm 1})}{T_2(\varepsilon^{\pm 2})} \quad (14)$$

$$dx_2 = \frac{dS_2 \cdot A_1 - dS_1 \cdot A_2}{B_2 \cdot A_1 - B_1 \cdot A_2} = \frac{T(\varepsilon^{\pm 2})}{T_2(\varepsilon^{\pm 3})} \quad (15)$$

Both these thicknesses being identical by definition, one has the following relation which the dielectric function must verify:

$$P(\in^{\pm 4}) = T(\in^{\pm 2})^2 - T_1(\in^{\pm 1}) \cdot T_2(\in^{\pm 3}) = 0 \quad (16)$$

The latter function is called "master function". This function is then multiplied by $\in^4$ in order to obtain a polynomial equation of order 8. This equation is then solved and the solutions are filtered with a view to keeping only the solutions which are physically significant. To do so, the solutions without any physical direction are eliminated since $\in$ should be real and strictly greater than 1. Moreover, the thickness dx calculated using $\in$ should be positive and the optical thickness should be smaller than $\lambda/4$. Finally, among the remaining solutions, the solution whereof the value is closest to experimental value is selected. To do so, for the different solutions a criterion $\sigma^2$ is determined:

$$\sigma^2 = \frac{(dS_1' - dS_1)^2}{\Delta S_1^2} + \frac{(dS_2' - dS_2)^2}{\Delta S_2^2} \quad (17)$$

where $dS'_{1,2}$ is the value calculated using $\in$, dx reconstructed, $dS_{1,2}$ are the experimental values and $\Delta S_{1,2}$ the errors on the measurement.

The solution with the smallest $\sigma^2$ is selected.

Once $\in$ determined, the value obtained in the equation (14) is injected in order to obtain the thickness dx.

Acquisition of the measurement at different wavelengths enables to impose the complementary condition according to which the thickness of the new layer must be equal for each of the wavelengths considered. One may for instance average the dx obtained for n acquisitions corresponding to the following wavelengths according to the formula:

$$<dx> = \frac{\sum_{i=1}^{N} \frac{dx_i}{\sigma_i^2}}{\sum_{i=1}^{N} \frac{1}{\sigma_i^2}} \quad (18)$$

where $\sigma_i^2$ is defined by the equation (17), for the wavelength i.

It is then possible to optimise the measurements of the dielectric function $\in$ pour each wavelength by using this value for the thickness and by minimising $\chi^2$ by the formula:

$$\chi^2 = |dS'_1(\in, <dx>) - dS_1|^2 + |dS'_2(\in, <dx>) - dS_2|^2 \quad (19)$$

The method, according to the invention, may also advantageously be used in the case of incoherent reflection of a transparent and thick substrate by using the equations (3).

In different particular embodiments having each its own advantages and liable to possible combinations, the method, according to the invention, may adopt the following forms:

A first particular embodiment considers the case where one of the measurements $dS_1$ or $dS_2$ is unusable for determination of the parameters x, $\in$. The method, according to the invention, requires indeed simultaneous measurement of the signals $dS_1$ and $dS_2$ in order to obtain the parameters x, $\in$ of the layers deposited. It may however prove for instance that the experimental noise is sufficient to make one of both measurements unusable. A solution consists then in developing the terms $dS_1$ and $dS_2$ respectively of the equations (12) and (13) to the second order as a function of time. This development is allowed since the development in dx contains terms of the second order. The terms $dS_1$ and $dS_2$ can then be written as:

$$dS_{1,2}(t) = A^t_{1,2} \cdot dt^2 + B^t_{1,2} \cdot dt$$

where $A_{1,2}$ and $B_{1,2}$ may be determined using the experimental measurement for the layer being deposited.

By assuming a constant deposition rate v=dx/dt, the following equation can be provided:

$$dS_{1,2}(t) = A^t_{1,2}/v^2 \cdot dx^2 + B^t_{1,2}/v \cdot dx$$

By identifying the factors of this equation with those of the equations (12) and (13) and by eliminating the deposition rate v, a new "master function" may be obtained:

$$P(\in^{\pm 2}) = A^t_{1,2} \cdot [B_{1,2}(\in^{\pm 1})]^2 - A_{1,2}(\in^{\pm 2}) \cdot [B^t_{1,2}]^2 = 0$$

By multiplying this function by $\in^2$, one obtains a polynomial of order 4 whereof the solution, obtained after suitable filtering of the roots of this equation according to the description above, gives $\in$ then dx.

In a second particular embodiment, it may prove also that the deposition rate v=dx/dt is not constant during the deposition or that its value is not known at the beginning of the deposition. There remains then to adapt dynamically the value of the reversing pitch so that its value is still optimum for good determination of the parameters x and $\in$. This dynamic correction procedure of the reversing pitch is based on the comparison of the values $dS_{1,2}$ with the respective values of the experimental noise $\Delta S^e$ and uncertainty bars on the theoretical values $\Delta S^t$. As soon as the values of the variations $dS_{1,2}$ measured between the latter point used for the inversion and the new point recorded, are greater than $\gamma \cdot \text{Max}(\Delta S^e, \Delta S^t)$, where $\gamma$ is a fitting parameter whereof the value determined experimentally ranges between 1.5 and 2, whereas the corresponding wavelength is kept for the reversal.

This criterion is verified independently for $S_1$ and $S_2$. If it is verified for both these signals, the digital reversal, according to the invention, is performed conventionally. If it is verified for only one of both signals, the ratio $dS_1/dS_2$ is then calculated. If the latter is close to 1, the corresponding wavelength is not kept for the reversal, if not, one should refer to the first particular embodiment mentioned above.

In a third particular embodiment, one considers the case where the film exhibits a low absorption rate. The couple of values $S_1$, $S_2$ obtained by the reversal method, according to the invention, is in such a case no more equal to the theoretical value required $S_1$, $S_2$. It is then necessary to include a correction procedure intended to avoid iterative repetition of these errors during successive reversal sequences. If this difference between theoretical and reconstructed values is noted dS, one may write close to the correct solution:

$$dS_1 = \frac{\partial S_1}{\partial \text{Re}\varepsilon} \cdot d\text{Re}\varepsilon + \frac{\partial S_1}{\partial \text{Im}\varepsilon} \cdot d\text{Im}\varepsilon + \frac{\partial S_1}{\partial x} \cdot dx \quad (20)$$

-continued
$$dS_2 = \frac{\partial S_2}{\partial \text{Re}\varepsilon} \cdot d\text{Re}\varepsilon + \frac{\partial S_2}{\partial \text{Im}\varepsilon} \cdot d\text{Im}\varepsilon + \frac{\partial S_2}{\partial x} \cdot dx \quad (21)$$

By writing dx=0 and by grouping in the equations (20) and (21) the real and imaginary parts, one may then write:

$$dS_1 = \text{Re}\left(\frac{\partial S_1}{\partial \text{Re}\varepsilon}\right) \cdot d\text{Re}\varepsilon + \text{Re}\left(\frac{\partial S_1}{\partial \text{Im}\varepsilon}\right) \cdot d\text{Im}\varepsilon$$

$$dS_2 = \text{Im}\left(\frac{\partial S_2}{\partial \text{Re}\varepsilon}\right) \cdot d\text{Re}\varepsilon + \text{Im}\left(\frac{\partial S_2}{\partial \text{Im}\varepsilon}\right) \cdot d\text{Im}\varepsilon$$

$dS_1$ and $dS_2$ being known, it is possible to deduce therefrom the value of the correction terms, $dre\in$ and $dlm\in$, for $\in$. One may then determine a new value of $(S_1, S_2)$. If the latter still does not correspond to the theoretical value required, said procedure is repeated until S is minimum.

In a last particular embodiment, the case where the method according to the invention gives no solution for a given wavelength $\lambda$ is processed. This may be the case, for instance, when calibration errors are added to the case, already critical, of the reversal realised for points where the thickness of the optical phase is close to multi pies of $2\pi$. To obtain a reasonable value for the index s and thus carry on the usage of the method, one may resort to the acquisition of measurements for neighbouring wavelengths of $\lambda$. If the material deposited enables such approximation, one may fit the values of the index $\in$ obtained for various wavelengths close to $\lambda$ by a dispersion law and thus trace the value $\in$ for the wavelength $\lambda$ considered.

The method of the invention has been subject to several implementations presented in the following examples underlining the quality of the results obtained:

EXAMPLE 1

The method has been implemented to calibrate the deposition of layers made of silicium nitride oxide in a plasma chamber. In a first stage, one has determined the refraction index reconstructed in relation to the time of deposition (FIG. 1), this figure also shows the molecular oxygen flux which has been modified during the deposition. The refraction index reconstructed has been determined at two different wavelengths.

The graphs showing the evolution of the refraction index reconstructed as a function of time of deposition exhibit similar general profile. An initial phase is observed first of all where the refraction index exhibits quick variation of its value to reach a constant value. This initial phase corresponds to the nucleation phase for growing a layer of nitride on its own. As soon as the refraction index has reached a constant value, the molecular oxygen flux is gradually increased until it reaches its maximum value. Starting with $t_1$=1500 s, i.e. as the molecular oxygen flux enters the chamber, clear correlation may be observed between the gradual diminution of the value of the reflective index and the gradual increase of the molecular oxygen flux. When the molecular oxygen flux has reached the limit value of 3 sccm, the reflective index does not vary any longer. The concentration in molecular oxygen in the chamber is then sufficient to oxide all the silane molecules.

Figure 2:
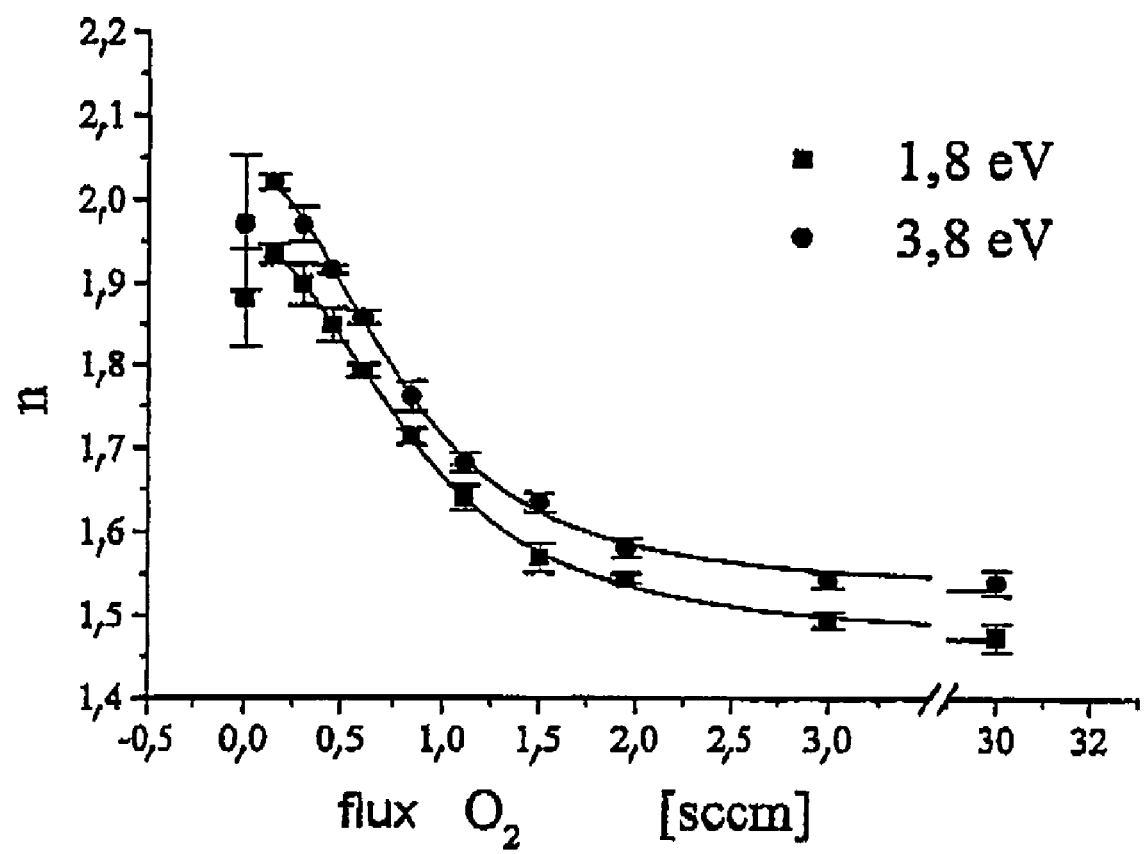
FIG. 2 represents the variation of the refraction index as a function of the molecular oxygen flux for two different wavelengths.

From such results, one has attempted to deduce therefrom the variation of the refraction index averaged over the individual layers (the time of deposition of said individual layers being fixed to 400 s) as a function of the molecular oxygen flux for two wavelengths (FIG. 2). The uncertainties on the mean value of the refractive index of each layer have been marked on the figure by error bars. These curves have then been fitted (solid lines) in order to deduce therefrom for each wavelength, a curve representing the variations of the refractive index as a function of the molecular oxygen flux. The growth ratio of the individual layers has been determined and fitted, similarly.

EXAMPLE 2

Figure 3:
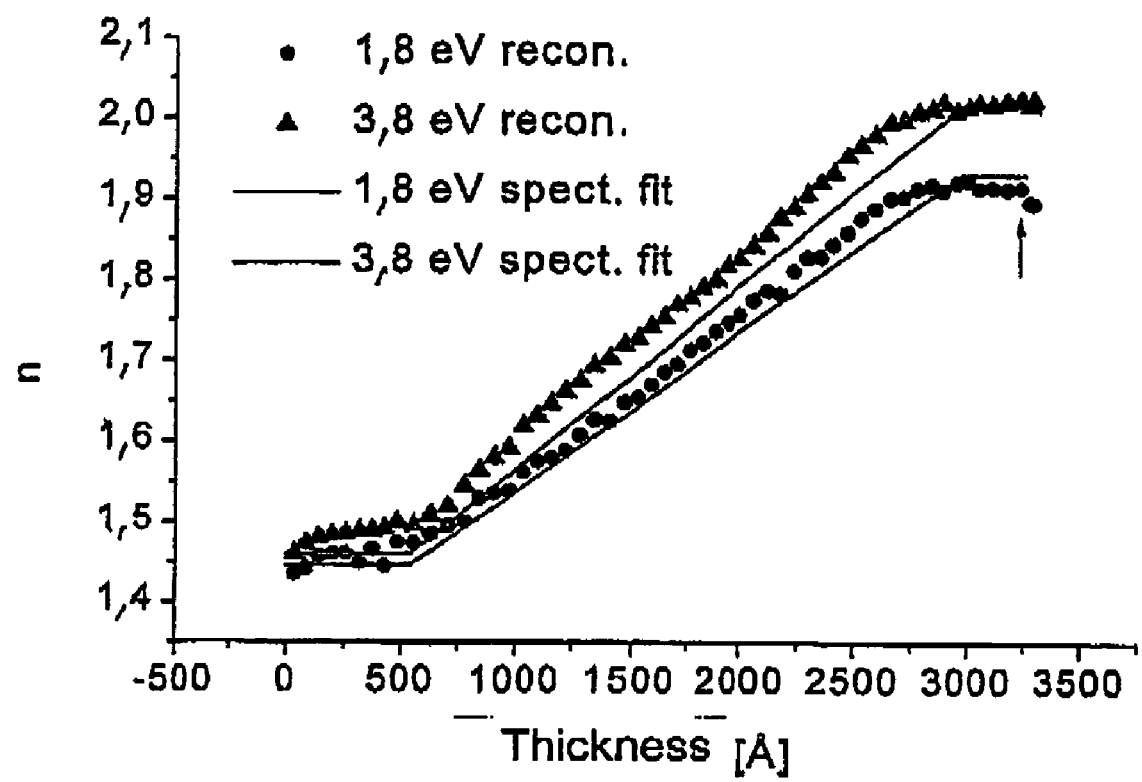
FIG. 3 represents the variation of the refraction index as a function of the thickness for two different wavelengths. The symbols correspond to the values reconstructed according to the present method and the lines are spectroscopic fittings.

The parameters determined in the example 1 have been used for the deposition on a glass surface of a layer exhibiting a linear increase of its refractive index. This stacking should contain, at its upper and lower ends, a layer of high and low index of a thickness 500 Å used as a reference index. On FIG. 3, one may observe that the total thickness reconstructed of the stacking after deposition is 3278 Å. It may be noticed that growth rate exhibits a profile quasi identical to that required, i.e. linear.

Figure 4:
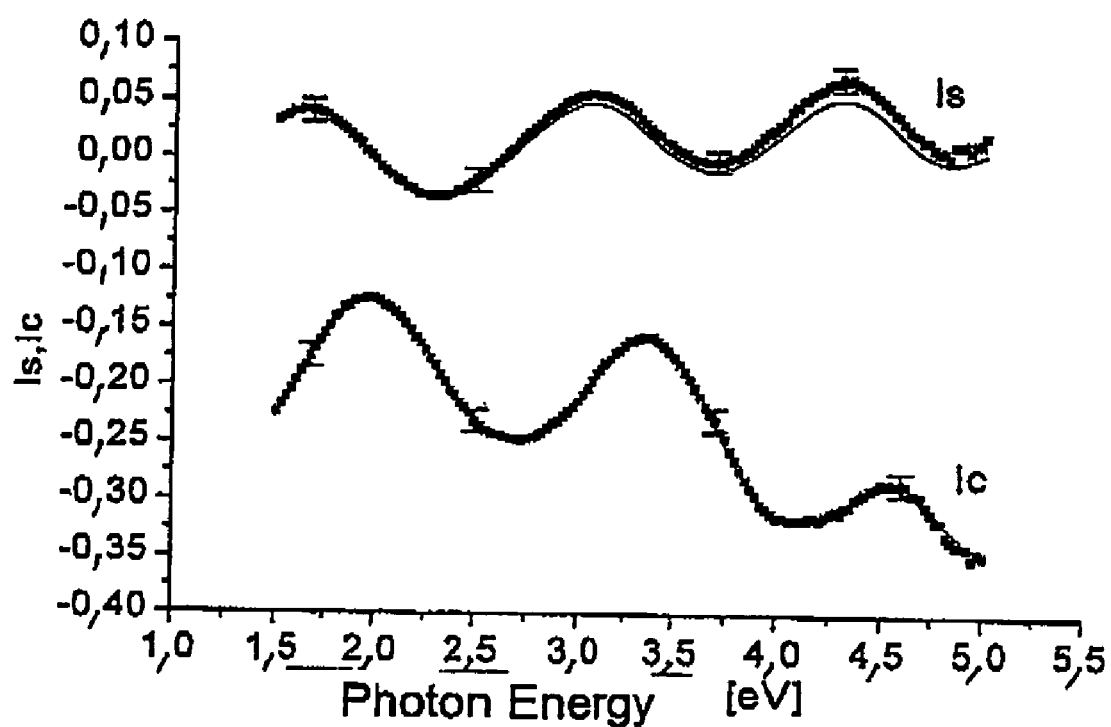
FIG. 4 is a comparison of the ellipsometric intensities Is and Ic obtained, either by measurements (symbols), or by spectroscopic fitting (solid line).

The curves of FIG. 4 correspond to the ellipsometric spectra measured after said deposition in the energy range 1.5 to 5 eV by varying the energy of the photons with a pitch of 0.025 eV. These curves have been modelled and fitted for a spectroscopic model in order to verify the index profile independently of the reversal method. The value of $\chi^2$ obtained and which measures the quality of the fitting, is 0.46. This value may be considered as excellent, especially for the ellipsometric intensity Ic which is, in this particular case, especially sensitive to the slope of the refractive index profile. The total thickness obtained by the fitting of the spectra measured, with 3253 Å, matches very well the result obtained by the method according to the invention, i.e. 3278 Å. The index profile found with such fitting (solid lines) is compared with the results of the method according to the invention. It can be noted that the value measured for the highest refractive index is very close to that obtained by the present method although the thickness of the corresponding layer is slightly smaller. Similarly, the index measured for the layer with the lowest refractive index is slightly smaller than that obtained by reconstruction. It should be noted, however, that the deviations between values obtained by fitting spectra measured and the profiles of reconstruction remain very low.

APPENDIX

| | |
|---|---|
| $\lambda$ | Wavelength |
| $k = 2\pi/\lambda$ | Wave number |
| S | Polarisation perpendicular to the plane of incidence |
| P | Polarisation parallel to the plane of incidence |
| $\epsilon$ | Complex dielectric constant |
| N | Optical (refraction) index |
| Dx | Thickness of a layer newly deposited on a stacking of layers |
| $r_s$ (respectively $r_p$) | Complex reflection coefficient for polarisation perpendicular (respectively parallel) to the plane of incidence |
| $dM_s$ (respectively $dM_p$) | Abeles matrix for a layer of thickness dx and for a polarisation perpendicular (respectively parallel) to the plane of incidence |
| $S_1, S_2$ | Optical signals measured |
| $dS_1, dS_2$ | Variation of the optical signals measured $S_1$ and $S_2$ for a layer of thickness dx newly deposited |
| $\Delta S_1, \Delta S_2$ | Experimental errors on the optical signals $S_1$ and $S_2$ |
| $\sigma^2$ | Standard deviation on $dS_1$, $dS_2$ between theoretical and experimental values |
| <dx> | Average value of the layer of thickness dx for N acquisitions at different wavelengths $\lambda$ |

The invention claimed is:

1. A characterisation or control method for preparation of a thin layer component according to optical methods wherein:

signals $S_1$ and $S_2$ related to the thickness x and to the complex optical index of the component for a wavelength $\lambda$ are measured and acquired, the signals $S_1$ and $S_2$ thus acquired are processed in order to obtain parameters x, $\in$ of the layers deposited, characterised in that:

the stacking is represented by the product of two Abeles matrices for each polarisation direction s (perpendicular to the plane of incidence) and p (parallel to the plane of incidence):

a matrix $Mo_{s,p}$ known representing the support, a matrix $dM_{s,p}$ representing a thin transparent layer being deposited, the inversion of the variations of the measured signals $dS_1$, $dS_2$ enables to get the thickness x and the dielectric constant $\in$ of the thin layer using the following operations:

Taylor development in relation to the variation dx of the thickness x of the thin layer of the coefficients of the matrix dM, calculation of the coefficients of the matrix $M_{s,p}$ each in the form $$A(\in^{\pm 2})dx^2 + B(\in^{\pm 1})dx + C$$

deducing therefrom the relation $$S_{1,2} = A_{1,2}(\in^{\pm 2})dx^2 + B_{1,2}(\in^{\pm 1})\,dx + C_{1,2}$$

linking the signals $S_1$ and $S_2$ to the parameters $\in$ and dx, eliminating dx, deducing therefrom a master function $$P(\in^{\pm 4}) = 0$$

solving the equation using an appropriate method, selecting the solutions of this equation corresponding to values physically plausible, to measure $\in$, using the value $\in$ obtained to determine dx.

2. A method according to claim 1, characterised in that the Taylor development is limited to the second order.

3. A method according to claim 1, characterised in that said method is applied during the deposition of the stacking and in that the evolution of $\in$ and/or $x_o$ is recorded.

4. A method according to claim 1, characterised in that said method is applied during the deposition of the stacking and in that the conditions of the deposition are influenced to interlock the parameters $\in$, x of the layers with the preset theoretical values.

5. A method according to claim 1, characterised in that the ellipsometer is phase-modulated generating the parameters $I_s$ and $I_c$.

6. A method according to claim 1, characterised in that the ellipsometer is fitted with a rotary polariser generating the parameters tan $\psi$, cos $\Delta$.

7. A method according to claim 1, characterised in that the thin layer is transparent.

8. A method according to claim 1, characterised in that the thin layer is absorbent.

9. Method according to claim 1, characterised in that the measurement is multiwavelength.

10. Method according to claim 9, characterised in that the thickness is optimised by averaging over the different wavelengths.

11. A method according to claim 10, characterised in that after optimising the thickness, the complex indices are re-calculated.

12. A method according to claim 1, characterised in that, if one of the measured signals $S_1$, $S_2$ is unusable, the other of the terms S1, S2 is developed to the second order in relation to time in the relation $S_1$, $S_2 = A_{1,2}(\in^{\pm 2})dx^2 + B_{1,2}(\in^{\pm 1})dx + C_{1,2}$ in order to determine new master function $P(\in^{\pm 2}) = 0$.

13. A method according to claim 1, characterised in that, if the deposition rate in the initial conditions of deposition is unknown or is not constant during the deposition, the value of the reversing pitch is adapted dynamically.

14. A method according to claim 1, characterised in that, for a film exhibiting a low absorption rate, attempt is made to minimise the deviation between required and reconstructed theoretical values.

15. A method according to claim 1, characterised in that, if no value is obtained for a given wavelength $\lambda$, the values of the index $\in$ obtained for various wavelengths close to $\lambda$ are processed to deduce therefrom the value of $\in$ for the wavelength $\lambda$ considered.

* * * * *